US00PP10668P

United States Patent [19]

Meilland

[11] Patent Number: Plant 10,668

[45] Date of Patent: Nov. 3, 1998

[54] HYBRID TEA ROSE PLANT NAMED 'MEINERAU'

[75] Inventor: Alain A. Meilland, Antibes, France

[73] Assignee: The Conard-Pyle Company, West Grove, Pa.

[21] Appl. No.: 796,580

[22] Filed: Feb. 6, 1997

[51] Int. Cl.[6] ..... A01H 5/00

[52] U.S. Cl. ..... Plt./15

[58] Field of Search ..... Plt./15, 11, 16

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive Chartreuse Yellow blossoms that are edged with Azalea Pink. Such blossoms commonly possess a configuration that resembles that of a peony blossom. The plant exhibits medium green and glossy foliage, as well as good disease resistance. The new variety is particularly well suited for growing as attractive ornamentation in the landscape.

3 Drawing Sheets

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the 'Sunblest' variety (non-patented in the United States) and the 'Korresia' variety (non-patented in the United States). The male parent (i.e., the pollen parent) was the 'Meinarval' variety (non-patented in the United States). The 'Meinarval' variety sometimes is known as the 'Sun King' variety. The parentage of the new variety can be summarized as follows:

('Sunblest'×'Korresia')×'Meinarval'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive Chartreuse Yellow blossoms that are edged with Azalea Pink and commonly assume a configuration resembling that of a peony blossom,
(b) exhibits a bushy and compact growth habit,
(c) forms attractive medium green and glossy foliage,
(d) exhibits good disease resistance, and
(d) is particularly well suited for growing as attractive ornamentation in the landscape.

The presence of the Azalea Pink edging on the petals of the blossoms is influenced by the growing conditions. For instance, when the plant is forced such Azalea Pink coloration may be substantially absent as illustrated in some of the photographs. Accordingly, when forced the blossoms tend to lack such edging and to assume a lighter yellow coloration across both surfaces of the petals.

The new variety well meets the needs of the horticultural industry and is particularly well adapted for use as an attractive ornamental plant in an outdoors environment.

Under such growing conditions the Azalea Pink edging of the blossoms petals commonly fully develops as illustrated in FIGS. 16 and 17.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety, and is being marketed under the CENTENNIAL STAR trademark has been named the 'Meinerau' variety.

BRIEF DESCRIPTION OF THE PHOTOGRAPHS

The accompanying photograph shows as nearly true as it is reasonably possible to make the same, in a color illustration of this character, typical specimens of the plant parts of the new variety. The rose plants of the new variety were two years of age and were observed during September (except in FIGS. 16 and 17) while budded on *Rosa froebelii* understock and growing outdoors at Le Cannet des Maures, Var, France. Such blossoms of FIGS. 4 through 9 were forced. Under such growing conditions the Azalea Pink edging of the petals often is not fully developed. The blossoms illustrated in FIGS. 16 and 17 were observed during the summer in the absence of forcing and well illustrate the propensity of the petals to become edged with Azalea Pink coloration. Dimensions in centimeters are indicated at the bottom of the photograph of FIGS. 1 to 15.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimen of leaves with three leaflets—plan view—upper surface (left) and under surface (right);

FIG. 15—illustrates a specimen of a leaf with five leaflets—plan view—upper surface;

FIG. 16—illustrates a perspective view of a typical blossom during the summer wherein the Azalea Pink edging of the petals is fully developed;

FIG. 17—illustrates a perspective view of a cluster of blossoms during the summer where the Azalea Pink edging of the petals, sepals, and foliage are apparent.

DETAILED DESCRIPTION

Figures 1, 2, 3, 4, 5, 6, 7, 8, 9, 10, 11, 12, 13, 14, 15:
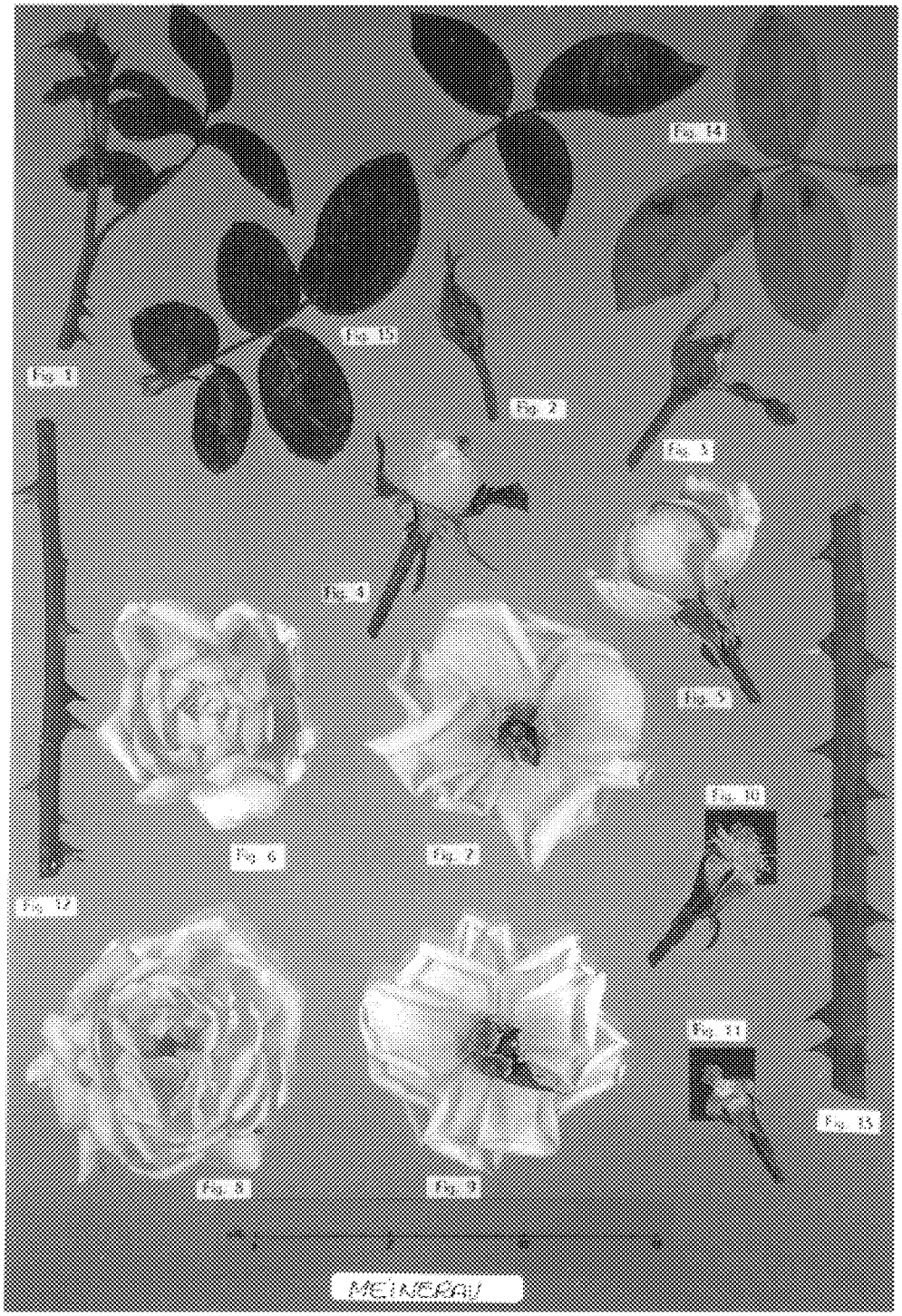
Figure 16:
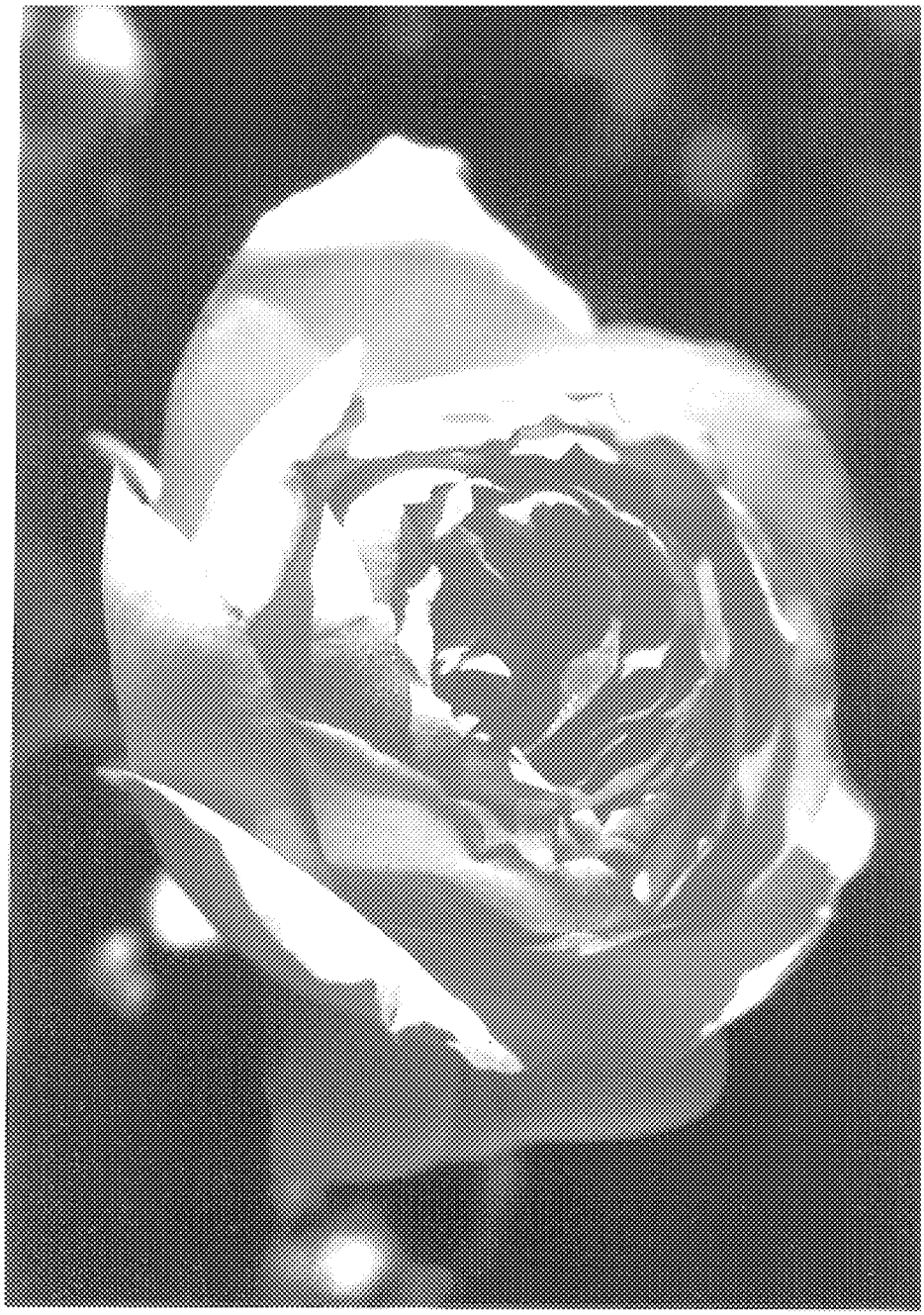
Figure 17:
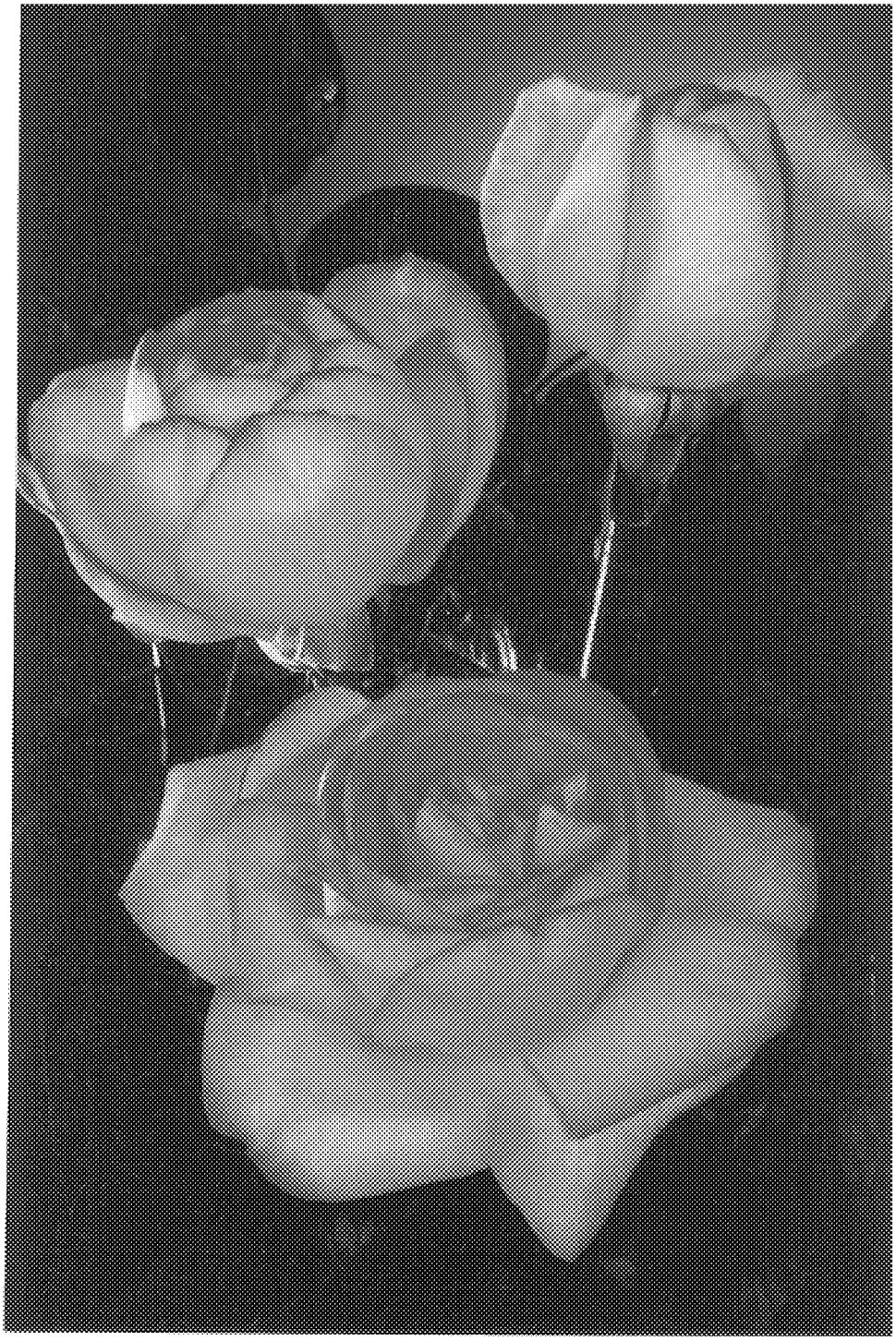

The chart used in the identification of the colors is that of The Royal Horticultural Society (R.H.S. Colour Chart). The description is based on the observation of two year-old plants during September while budded on *Rosa froebelii* understock and growing outdoors at Le Cannet des Maures, Var, France. The coloration in common terms precedes reference to the chart in some instances.

Class: Hybrid Tea.

Plant:

*Height*.—Approximately 90 to 100 cm. on average at the end of the growing season. Flower stem lengths of approximately 30 to 45 cm. commonly are formed.

*Habit*.—Bushy.

Branches:

*Color*.—Young stems: Yellow-Green Group 146B, and widely suffused with reddish-brown coloration. Adult wood: Yellow-Green Group 146B.

*Thorns*.—Size: medium. Quantity: moderately numerous to numerous.

Color: Yellow-Orange Group 20B with highlights of Red Group 39C on young stems and Havana Brown (near Greyed-Orange Group 176C) on adult wood.

Leaves:

*Stipules*.—Adnate, pectinate, and moderately broad.

*Petioles*.—Upper surface: striped reddish on young foliage, and medium green (commonly between Green Group 143B and 143C) on adult foliage and glandular. Under surface: medium green, and aciculate with small thorns.

*Leaflets*.—Number: 3, 5, and 7 (most often). Shape: elliptic. Serration: simple and regular (as illustrated). Size: average to large for the class. Texture: consistent. General appearance: medium green, and glossy. Color (young foliage): upper surface: Green Group 137A and widely suffused with reddish brown. Under surface: Green Group 137C suffused wth reddish brown. Color: (adult foliage): upper surface: Green Group 137A. under surface: bronze green, Greyed-Green Group 191A.

Inflorescence:

*Number of flowers*.—Usually one per stem.

*Peduncle*.—Light green (Green Group 143C) with some reddish coloration, and the length is approximately 8.5 cm. on average very strong, commonly without bent necks, rough and with some relatively soft prickles.

*Sepals*.—Upper surface: tomentose, and greenish (Greyed-Green Group 149B) in coloration.

Under surface: light green (commonly between Green Group 138A and 138B) in coloration and with some extensions.

*Buds*.—Shape: conical. Length: Approximately 3 cm. on average. Size: large. Color upon opening: upper surface: Chartreuse Yellow, Yellow Group 2B, and lightly edged with Azalea Pink, Red Group 38B. under surface: Chartreuse Yellow, Yellow Group 2B, and lightly edged with Azalea, Red Group 38B.

*Flower*.—Shape: cup-shaped with a round center. Diameter: approximately 12 cm. on average. Color: (when opening begins): upper surface: Naples Yellow, Yellow Group 11A, and lightly edged with Azalea Pink, Red Group 38B. under surface: Naples Yellow, Yellow Group 11A, and lightly edged with Azalea Pink, Red Group 38B, Color (when blooming): upper surface: Naples Yellow, Yellow Group 11A, and lightly edged with Azalea Pink, Red Group 38B. under surface: Naples Yellow, Yellow Group 11A, and lightly edged with Azalea Pink, Red Group 38B. Color (at end of opening): upper surface: Naples Yellow, Yellow Group 11A, and lightly edged with Azalea Pink, Red Group 38B. under surface: Naples Yellow, Yellow Group 11A, and lightly edged with Azalea Pink, Red Group 38B. Lasting quality: commonly approximately 7 to 10 days on the plant and approximately 3 to 5 days when cut and placed in a vase. Fragrance: absent. Petal number: approximately 50 on average. Petal shape: the base is obtuse and the tip is rounded with reflexed edges. Petal texture: consistent. Stamen number: approximately 80 on average. Anthers: ochre in coloration. Filaments: yellow in coloration. Pistil number: approximately 50 on average. Stigmas: yellow in coloration. Styles: pinkish-yellow in coloration. Receptacle: medium green, suffused with reddish-brown coloration, and in longitudinal section in the shape of a funnel.

Development:

*Vegetation*.—Strong.

*Blooming*.—Abundant and substantially continuous.

*Resistance to diseases*.—Good, particularly with respect to powdery mildew and downey mildew.

*Resistance to frost*.—Average.

*Propensity to form seed/hips*.—Absent.

I claim:

1. A new and distinct variety of Hybrid Tea rose plant characterized by the following combination of characteristics:

(a) forms in abundance attractive Chartreuse Yellow blossoms that are edged with Azalea Pink and commonly assume a configuration resembling that of a peony blossom, (b) exhibits a bushy and compact growth habit, (c) forms attractive medium green and glossy foliage, (d) exhibits good disease resistance, and (e) is particularly well suited for growing as attractive in the ornamentation in the landscape;

substantially as herein shown and described.

* * * * *